(12) United States Patent
Fan et al.

(10) Patent No.: US 9,943,279 B2
(45) Date of Patent: Apr. 17, 2018

(54) METHODS AND SYSTEMS FOR TASK-BASED DATA GENERATION AND WEIGHTING FOR CT SPECTRAL IMAGING

(71) Applicant: General Electric Company, Schenectady, NY (US)

(72) Inventors: Jiahua Fan, New Berlin, WI (US); Jie Tang, Pewaukee, WI (US); Hewei Gao, Pewaukee, WI (US)

(73) Assignee: General Electric Company, Schenectady, NY (US)

( * ) Notice: Subject to any disclaimer, the term of this patent is extended or adjusted under 35 U.S.C. 154(b) by 555 days.

(21) Appl. No.: 14/520,204

(22) Filed: Oct. 21, 2014

(65) Prior Publication Data

US 2016/0106386 A1 Apr. 21, 2016

(51) Int. Cl.
*A61B 6/00* (2006.01)
*A61B 6/03* (2006.01)
*G06T 11/00* (2006.01)

(52) U.S. Cl.
CPC ............. *A61B 6/482* (2013.01); *A61B 6/032* (2013.01); *A61B 6/5235* (2013.01); *G06T 11/008* (2013.01); *A61B 6/037* (2013.01); *A61B 6/5258* (2013.01); *G06T 2211/408* (2013.01)

(58) Field of Classification Search
CPC .. A61B 6/482; A61B 6/5235; G06T 2211/408
See application file for complete search history.

(56) References Cited

U.S. PATENT DOCUMENTS

| | | | |
|---|---|---|---|
| 7,792,241 B2 | 9/2010 | Wu et al. | |
| 7,826,587 B1 | 11/2010 | Langan et al. | |
| 7,995,702 B2 | 8/2011 | Xu et al. | |
| 8,306,180 B2 | 11/2012 | Zhang et al. | |
| 8,787,519 B2 | 7/2014 | Fan et al. | |
| 2011/0158498 A1* | 6/2011 | Li | G06T 11/008 382/132 |
| 2012/0039440 A1* | 2/2012 | Fan | A61B 6/032 378/62 |
| 2013/0202178 A1 | 8/2013 | Shechter | |
| 2013/0308745 A1 | 11/2013 | Goshen | |

* cited by examiner

*Primary Examiner* — Dani Fox
(74) *Attorney, Agent, or Firm* — McCoy Russell LLP

(57) ABSTRACT

Various methods and systems for weighting material density images based on the material imaged are disclosed. In one embodiment, a method for dual energy imaging of a material comprises generating an odd material density image, generating an even material density image, applying a first weight to the odd material density image and a second weight to the even material density image, and generating a material density image based on a combination of the weighted odd material density image and the weighted even material density image. In this way, the image quality may be improved without increasing a radiation dosage.

18 Claims, 7 Drawing Sheets

METHODS AND SYSTEMS FOR TASK-BASED DATA GENERATION AND WEIGHTING FOR CT SPECTRAL IMAGING

FIELD

Embodiments of the subject matter disclosed herein relate to diagnostic imaging, and more particularly, to image reconstruction for dual energy spectral imaging.

BACKGROUND

Dual or multi-energy spectral computed tomography (CT) systems can reveal the densities of different materials in an object and generate images acquired at multiple monochromatic x-ray energy levels. In the absence of object scatter, a system derives the behavior at a different energy based on a signal from two regions of photon energy in the spectrum: the low-energy and the high-energy portions of the incident x-ray spectrum. In a given energy region of medical CT, two physical processes dominate the x-ray attenuation: Compton scattering and the photoelectric effect. The detected signals from two energy regions provide sufficient information to resolve the energy dependence of the material being imaged. Detected signals from the two energy regions provide sufficient information to determine the relative composition of an object composed of two hypothetical materials.

Different approaches have been developed to realize dual energy or spectral imaging. To name a few, dual x-ray source and detector, single x-ray source and detector with multiple acquisitions at different peak kilovoltage (kVp) or interleaved with fast kVp switching capability, and single x-ray source with an energy discriminative detector are leading techniques. In a single x-ray source and detector arrangement, a conventional third generation CT system may acquire projections sequentially at different kVp levels, which changes the peak and spectrum of energy of the incident photons comprising the emitted x-ray beams. Two scans are acquired—either back-to-back sequentially in time where the scans require two rotations around the subject, hereinafter referred to as rotate-rotate dual energy, or interleaved as a function of the rotation angle requiring one rotation around the subject, hereinafter referred to as fast-switching dual energy, in which the x-ray tube operates, for instance, at 80 kVp and 140 kVp potentials.

Once dual or multi-energy data is obtained, a basis material decomposition (BMD) algorithm may be applied in order to image two distinct materials, such as water and iodine, as examples. A conventional BMD algorithm is based on the concept that, in an energy region for medical CT, the x-ray attenuation of any given material can be represented by a proper density mix of two materials with distinct x-ray attenuation properties, referred to as the basis materials. The BMD algorithm computes two material density images that represent the equivalent density of one of the basis materials based on the measured projections at high and low x-ray photon energy spectra, respectively. The material density images may be further converted to form monochromatic images at other desired monochromatic energies.

Typically the measured projections at high and low x-ray photon energy spectra are equally treated when generating material density images. However, the x-ray attenuation properties of the basis materials may affect the material density differently at different energy levels. Furthermore, fast-switching dual energy CT systems may interpolate high and low energy projection data to obtain complete projection datasets, potentially introducing noise to the data. As a result, material density images and subsequently formed monochromatic images may feature a degraded image quality due to an unnecessary dependence on interpolated data.

BRIEF DESCRIPTION

In one embodiment, a method for dual energy imaging of a material comprises generating an odd material density image, generating an even material density image, applying a first weight to the odd material density image and a second weight to the even material density image, and generating a material density image based on a combination of the weighted odd material density image and the weighted even material density image. In this way, the image quality may be improved without increasing a radiation dosage.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

The following description relates to various embodiments of image reconstruction for dual energy spectral imaging. In particular, methods and systems for weighting material density images based on the material imaged are disclosed. The operating environment of the present invention is described with respect to a sixty-four-slice computed tomography (CT) system, such as the CT imaging system shown in FIGS. 1-4. However, it will be appreciated by those skilled in the art that the invention is equally applicable for use with other multi-slice configurations. Moreover, the invention will be described with respect to the detection and conversion of x-rays. However, one skilled in the art will further appreciate that the invention is equally applicable for the detection and conversion of other high frequency electromagnetic radiation. The invention will be described with respect to a "third generation" CT scanner, but is equally applicable with other CT systems.

Figure 1:
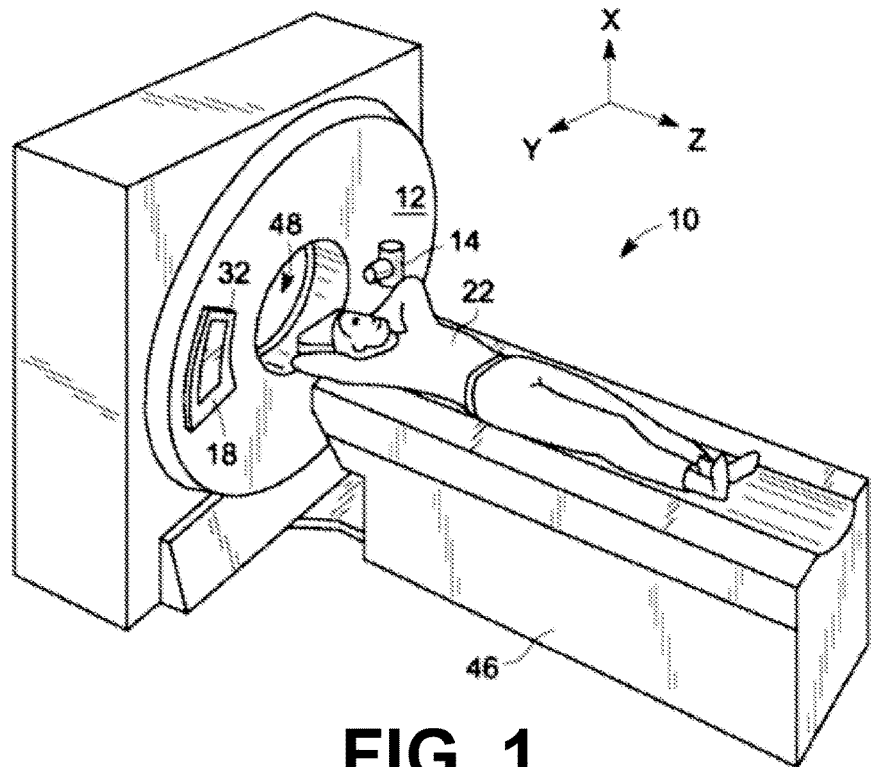
FIG. 1 is a pictorial view of an imaging system according to an embodiment of the invention.
Figure 2:
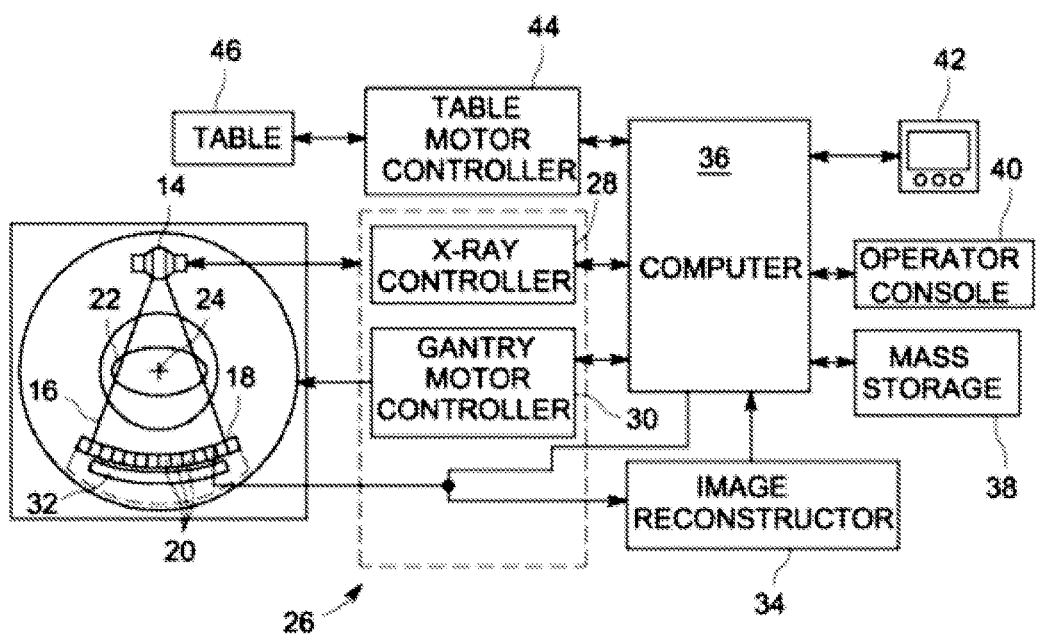
FIG. 2 is a block schematic diagram of an exemplary imaging system according to an embodiment of the invention.

Referring to FIGS. 1 and 2, a CT imaging system 10 is shown as including a gantry 12 representative of a "third generation" CT scanner. Gantry 12 has an x-ray source 14 that projects a beam of x-rays 16 toward a detector assembly or collimator 18 on the opposite side of the gantry 12. Detector assembly 18 is formed by a plurality of detectors 20 and data acquisition system (DAS) 32. The plurality of detectors 20 sense the projected x-rays that pass through a medical patient 22, and DAS 32 converts the data to digital signals for subsequent processing. Each detector 20 produces an analog electrical signal that represents the intensity of an impinging x-ray beam and hence the attenuated beam as it passes through the patient 22. During a scan to acquire x-ray projection data, gantry 12 and the components mounted thereon rotate about a center of rotation 24.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. An image reconstructor 34 receives sampled and digitized x-ray data from DAS 32 and performs high speed reconstruction. The reconstructed image is applied as an input to a computer 36 which stores the image in a mass storage device 38.

Computer 36 also receives commands and scanning parameters from an operator via console 40 that has some form of operator interface, such as a keyboard, mouse, voice activated controller, or any other suitable input apparatus. An associated display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44 which controls a motorized table 46 to position patient 22 and gantry 12. Particularly, table 46 moves patient 22 through a gantry opening 48 of FIG. 1 in whole or in part.

Figure 3:
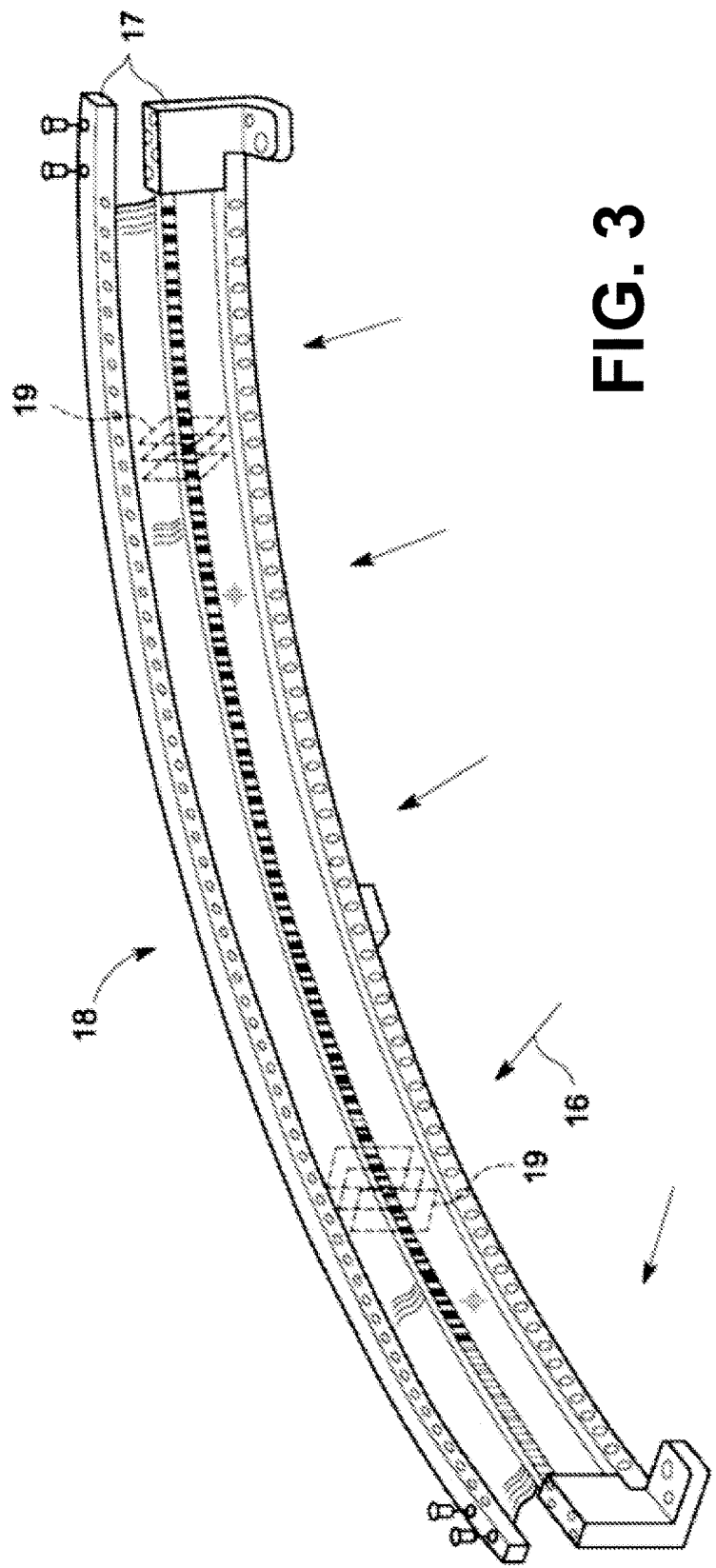
FIG. 3 is a perspective view of one embodiment of a CT system detector array.

As shown in FIG. 3, detector assembly 18 includes rails 17 having collimating blades or plates 19 placed therebetween. Plates 19 are positioned to collimate x-rays 16 before such beams impinge upon, for instance, detector 20 of FIG. 4 positioned on detector assembly 18. In one embodiment, detector assembly 18 includes 57 detectors 20, each detector 20 having an array size of 64×16 of pixel elements 50. As a result, detector assembly 18 has 64 rows and 912 columns (16×57 detectors), which allows 64 simultaneous slices of data to be collected with each rotation of gantry 12.

Figure 4:
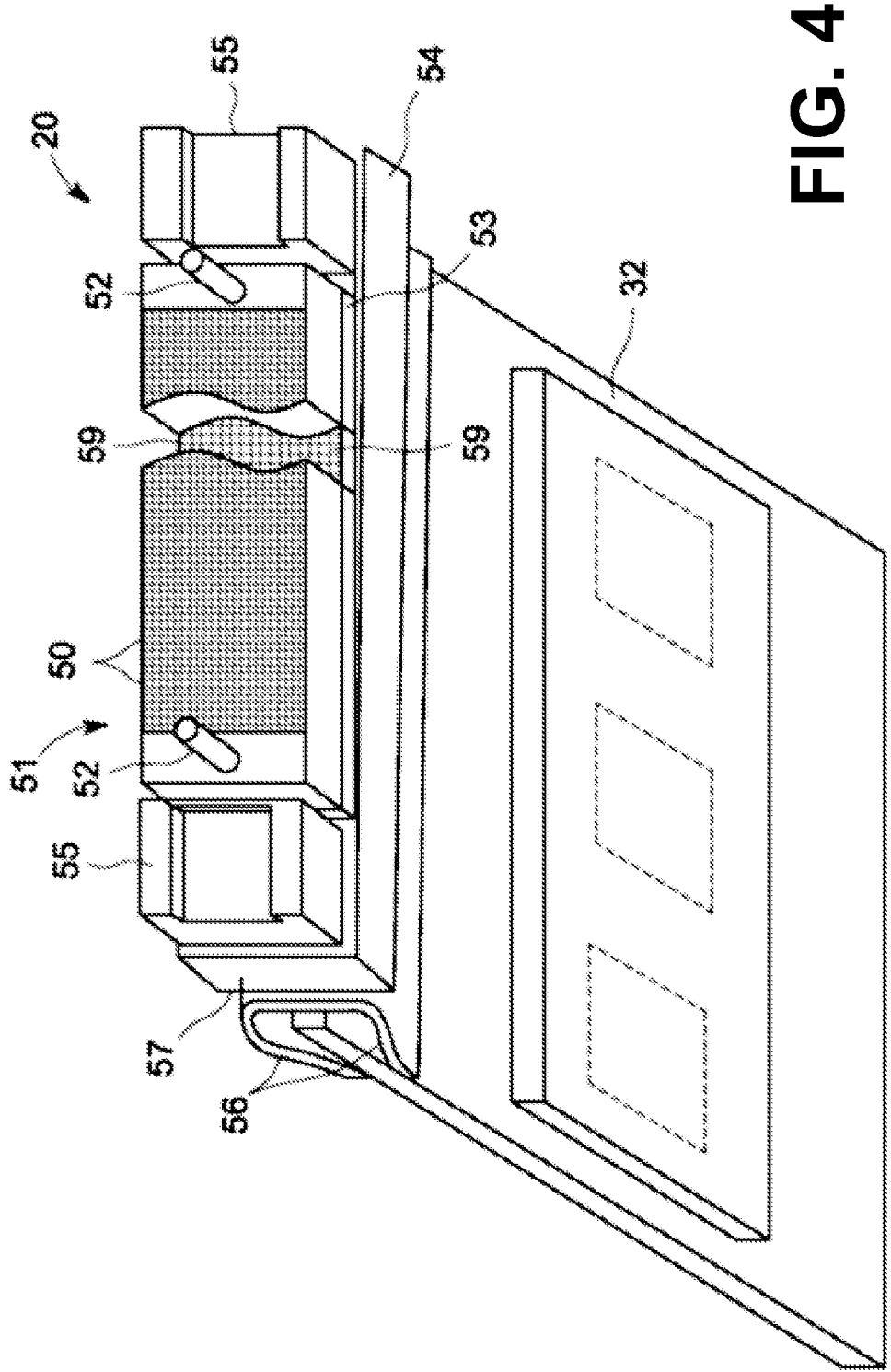
FIG. 4 is a perspective view of one embodiment of a CT detector.

Referring to FIG. 4, detector 20 includes DAS 32, with each detector 20 including a number of detector elements 50 arranged in pack 51. Detectors 20 include pins 52 positioned within pack 51 relative to detector elements 50. Pack 51 is positioned on a backlit diode array 53 having a plurality of diodes 59. Backlit diode array 53 is in turn positioned on multi-layer substrate 54. Spacers 55 are positioned on multi-layer substrate 54. Detector elements 50 are optically coupled to backlit diode array 53, and backlit diode array 53 is in turn electrically coupled to multi-layer substrate 54. Flex circuits 56 are attached to face 57 of multi-layer substrate 54 and to DAS 32. Detectors 20 are positioned within detector assembly 18 by use of pins 52.

In the operation of one embodiment, x-rays impinging within detector elements 50 generate photons which traverse pack 51, thereby generating an analog signal which is detected on a diode within backlit diode array 53. The analog signal generated is carried through multi-layer substrate 54, through flex circuits 56, to DAS 32 wherein the analog signal is converted to a digital signal.

As described above, each detector 20 may be designed to directly convert radiographic energy to electrical signals containing energy discriminatory or photon count data. Thus, in an alternate preferred embodiment, each detector 20 includes a semiconductor layer fabricated from CZT. Each detector 20 also includes a plurality of metallized anodes attached to the semiconductor layer. Such detectors 20 may include an electrical circuit having multiple comparators thereon which may reduce statistical error due to pileup of multiple energy events.

Referring back to FIGS. 1 and 2, a discussion is now presented in connection with a decomposition algorithm. An image or slice is computed which may incorporate, in certain modes, less or more than 360 degrees of projection data to formulate an image. The image may be collimated to desired dimensions using tungsten blades in front of the x-ray source and different detector apertures. A collimator typically defines the size and shape of the beam of x-rays 16 that emerges from the x-ray source 14, and a bowtie filter may be included in the system 10 to further control the dose to the patient 22. A typical bowtie filter attenuates the beam of x-rays 16 to accommodate the body part being imaged, such as head or torso, such that, in general, less attenuation is provided for x-rays passing through or near an isocenter of the patient 22. The bowtie filter shapes the x-ray intensity during imaging in accordance with the region-of-interest (ROI), field of view (FOV), and/or target region of the patient 22 being imaged.

As the x-ray source 14 and the detector array 18 rotate, the detector array 18 collects data of the attenuated x-ray beams. The data collected by the detector array 18 undergoes pre-processing and calibration to condition the data to represent the line integrals of the attenuation coefficients of the scanned object or the patient 22. The processed data are commonly called projections.

Figure 5:
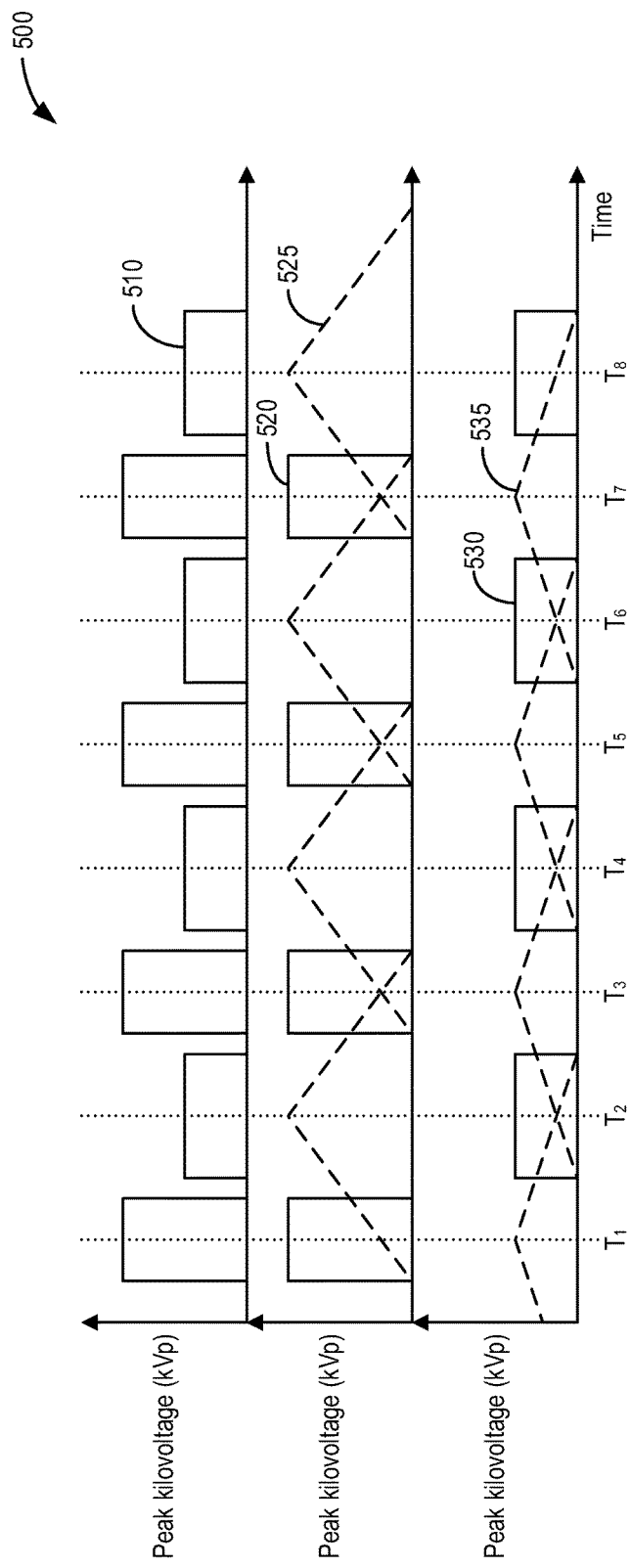
FIG. 5 shows a set of graphs illustrating an example data acquisition and interpolation scheme according to an embodiment of the invention.

In dual or multi-energy imaging, two or more sets of projection data are typically obtained for the imaged object at different tube peak kilovoltage (kVp) levels, which change the peak and spectrum of energy of the incident photons comprising the emitted x-ray beams or, alternatively, at a single tube peak kilovoltage (kVp) level or spectrum with an energy resolving detector of the detector array 18. For example, as shown by fast-switching kVp data acquisition scheme depicted by plot 510 in FIG. 5, tube peak kVp levels may rapidly alternate between high and low kVp levels during a single scan. Data interpolation may be applied to the acquired high kVp datasets and the low kVp datasets to provide complete datasets for both high kVP and low kVp. For example, as shown by the graphs 500 in FIG. 5, plot 525 illustrates interpolated data for the high kVp data 520 while plot 535 illustrates interpolated data for the low kVp data 530. The full datasets, including the interpolated data, may be temporally aligned to form pairs of data. For example, at time $T_1$, the acquired data may comprise a measured high kVp data point and an interpolated low kVp data point. At time $T_2$, the acquired data may comprise an interpolated high kVp data point and a measured low kVp data point. Similar aligned pairs of interpolated and measured kVp data are located at times $T_3$, $T_4$, $T_5$, and so on, as shown in FIG. 5. A measured high kVp data point and an interpolated low kVp data point may be referred to hereinafter as a type 1 pair, or an odd pair. Similarly, an interpolated high kVp data point and a measured low kVp data point may be referred to hereinafter as a type 2 pair, or an even pair.

The acquired sets of projection data may be used for basis material decomposition (BMD). During BMD, the measured projections are converted to a set of density line-integral projections. The density line-integral projections may be reconstructed to form a density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the CT system 10 reveals internal features of the patient 22, expressed in the densities of the two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In addition to a CT number or Hounsfield value, an energy selective CT system can provide additional information related to a material's atomic number and density. This information may be particularly useful for a number of medical clinical applications, where the CT number of different materials may be similar but the atomic number may be quite different. For example, calcified plaque and iodine-contrast enhanced blood may be located together in coronary arteries or other vessels. As will be appreciated by those skilled in the art, calcified plaque and iodine-contrast enhanced blood are known have distinctly different atomic numbers, but at certain densities these two materials are indistinguishable by CT number alone.

A decomposition algorithm is employable to generate atomic number and density information from energy sensitive x-ray measurements. Multiple energy techniques comprise dual energy, photon counting energy discrimination, dual layered scintillation and/or one or more other techniques designed to measure x-ray attenuation in two or more distinct energy ranges. As an example, a compound or mixture of materials measured with a multiple energy technique may be represented as a hypothetical material having the same x-ray energy attenuation characteristics. This hypothetical material can be assigned an effective atomic number Z. Unlike the atomic number of an element, effective atomic number of a compound is defined by the x-ray attenuation characteristics, and it needs not be an integer. This effective Z representation property stems from a well-known fact that x-ray attenuation in the energy range useful for diagnostic x-ray imaging is strongly related to the electron density of compounds, which is also related to the atomic number of materials.

The basis for the present disclosure is the consistency of the attenuation coefficient of water at high and low energies. For dual energy data acquisition, typically water and iodine are chosen as two basis materials. The data acquisition process may be described using a pair of equations for intensity measurements of the high and low spectra:

$$I_H = \int S_H(E) \cdot e^{-D_w \cdot (\frac{\mu}{\rho})_w(E)} \cdot e^{-D_I \cdot (\frac{\mu}{\rho})_I(E)} \cdot dE,$$

$$I_L = \int S_L(E) \cdot e^{-D_w \cdot (\frac{\mu}{\rho})_w(E)} \cdot e^{-D_I \cdot (\frac{\mu}{\rho})_I(E)} \cdot dE,$$

where $I_H$ and $I_L$ are the respective intensity measurements from the high and low spectra, $S_H(E)$ and $S_L(E)$ are the respective incident high and low x-ray spectra, $D_w$ and $D_I$ are the respective water and iodine material densities, and $(\mu/\rho)_w$ and $(\mu/\rho)_I$ are the respective mass attenuation functions of water and iodine.

The material decomposition may be described using the matrix below:

$$\begin{pmatrix} P_H \\ P_L \end{pmatrix} = \begin{pmatrix} \mu_{w\_H} & \mu_{I\_H} \\ \mu_{w\_L} & \mu_{I\_L} \end{pmatrix} \cdot \begin{pmatrix} D_w \\ D_I \end{pmatrix},$$

where $P_H$ and $P_L$ are the projection data measurements at high and low energies, $\mu_{w\_H}$ and $\mu_{w\_L}$ are the equivalent attenuation coefficients of water at high and low energy settings, $\mu_{I\_H}$ and $\mu_{I\_L}$ are the equivalent attenuation coefficients of iodine at high and low energy settings. At first order, the attenuation coefficient of water remains constant between high and low energies. Then the material densities may be calculated as:

$$D_w = \frac{P_H \cdot \mu_{I\_L} - P_L \cdot \mu_{I\_H}}{\mu_{w\_H} \cdot \mu_{I\_L} - \mu_{w\_L} \cdot \mu_{I\_H}} = \frac{P_H \cdot \mu_{I\_L} - P_L \cdot \mu_{I\_H}}{(\mu_{I\_L} - \mu_{I\_H}) \cdot \mu_w},$$

$$D_I = \frac{-(P_H \cdot \mu_{I\_L} - P_L \cdot \mu_{w\_H})}{\mu_{w\_H} \cdot \mu_{I\_L} - \mu_{w\_L} \cdot \mu_{I\_H}} = \frac{(P_L - P_H) \cdot \mu_w}{(\mu_{I\_L} - \mu_{I\_H}) \cdot \mu_w} = \frac{P_L - P_H}{\mu_{I\_L} - \mu_{I\_H}},$$

where each expression is simplified by the assumption that the attenuation coefficients for water at high and low energy settings are equal, or $\mu_{w\_L} = \mu_{w\_H} = \mu_w$. The above expressions for material densities reveal that the material density for water $D_w$ is dominated by the projection data at high energies $P_H$ while the material density for iodine $D_I$ is dominated by the projection data at low energies $P_L$. As a result, the image quality, in particular the resolution and noise properties, of material density images generated using even pairs may differ the image quality of material density images generated using odd pairs. For example, given that the material density for water $D_w$ is dominated by projection data at high energies $P_H$, water density images generated using odd pairs, or pairs of measured high kVp data and interpolated low kVp data, may possess a higher image quality than water density images generated using even pairs, or pairs of measured low kVp data and interpolated high kVp data. Similarly, iodine density images generated using even pairs may possess a higher image quality than iodine density images generated using odd pairs.

In one embodiment, the material density images $D_w$ and $D_I$ may be generated using the following weighting scheme:

$$D_w = w_1 \cdot D_{w1} + (1-w_1) \cdot D_{w2},$$

$$D_I = w_2 \cdot D_{I1} + (1-w_2) \cdot D_{I2},$$

where $w_1$ and $w_2$ are weighting functions with a value in the range from zero to one, $D_{w1}$ and $D_{I1}$ are the water and iodine density images generated using type 1 or odd pairs, and $D_{w2}$ and $D_{I2}$ are the water and iodine density images generated using type 2 or even pairs. If the weighting functions are equal and in the middle of the range, i.e., $w_1=w_2=0.5$, then material density images generated using odd pairs and material density images generated using even pairs are equally used to generate basis material density images.

In one embodiment, a weighting function may be determined according to a dependency of a material density on high and low energy projection data. For example, water density images $D_w$ may be weighted towards odd water density images $D_{w1}$ by setting the weighting function $w_1$ equal to one. In such an example, the contribution of the even water density image $D_{w2}$ to a water density image $D_w$ may be reduced to 0% while the contribution of the odd water density image $D_{w1}$ to the water density image $D_w$ may be 100%. In other examples, the weighting function $w_1$ may be less than one. For example, the weighting function $w_1$ may be set to 0.75 such that the even water density image $D_{w2}$ comprises 25% of the water density image $D_w$ while the odd water density image $D_{w1}$ comprises 75% of the water density image $D_w$. As another example, iodine density images $D_I$ may be weighted towards even iodine density image $D_{I2}$ by setting the weighting function $w_2$ equal to one such that the even iodine density image $D_{I2}$ comprises 100% of the iodine density image $D_I$ while the odd iodine density image $D_{I1}$ comprises 0% of the iodine density image $D_I$. In other examples, the weighting function $w_2$ may be less than one.

Figure 6:
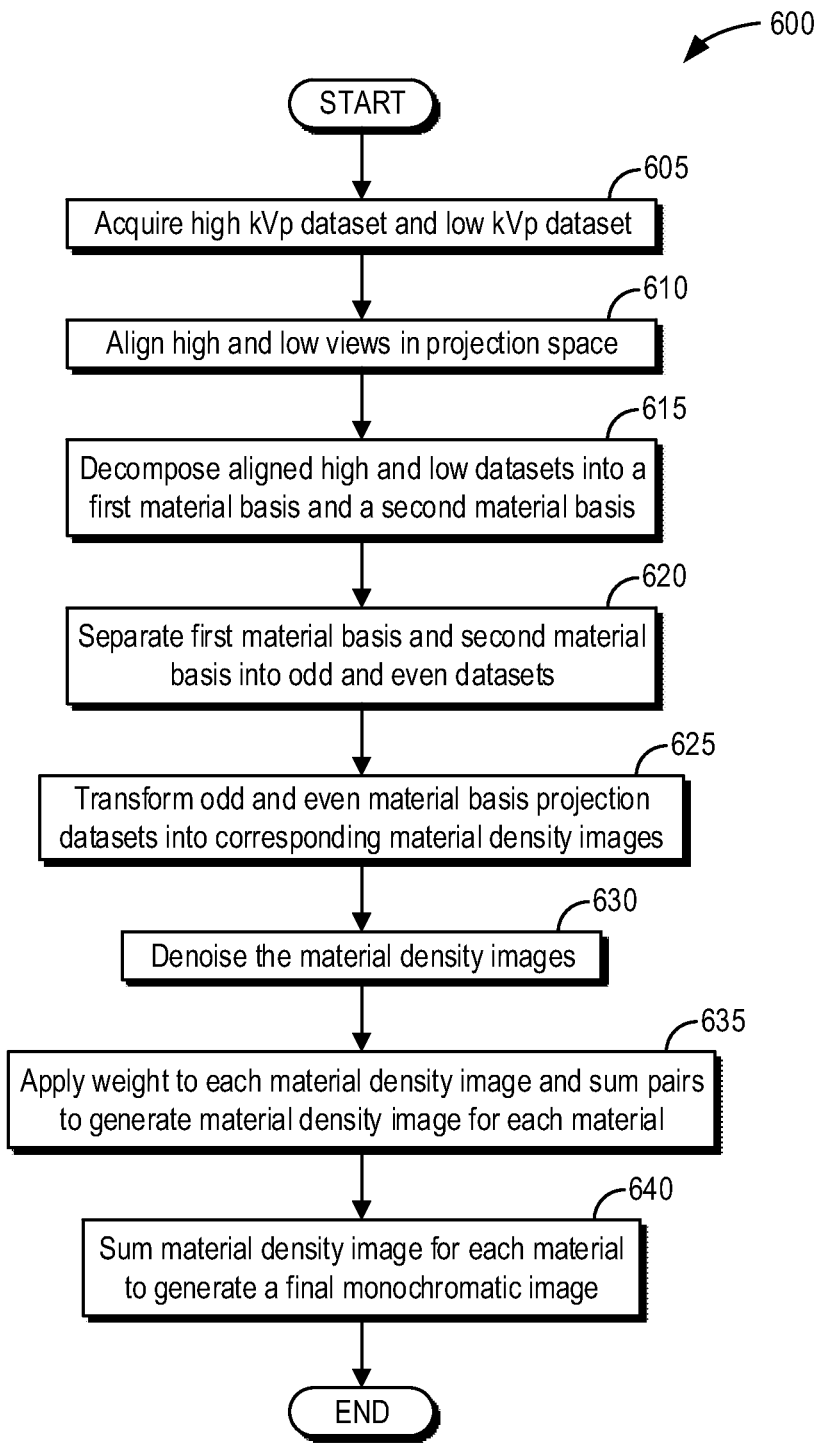
FIG. 6 shows a high-level flow chart illustrating an example method for generating a monochromatic image according to an embodiment of the invention.

FIG. 6 shows a high-level flow chart illustrating an example method 600 for generating a monochromatic image according to an embodiment of the invention. In particular, method 600 relates to generating a monochromatic image from material density images that are weighted based on contributions from high and low kVp projection data. Method 600 may be described with reference to the system and components shown in FIGS. 1 through 4, however the method may be applied to other systems without departing from the scope of the present disclosure. Method 600 may be carried out by image reconstructor 34 and may be stored as executable instructions in non-transitory memory of mass storage 38.

At 605, method 600 may include acquiring a high kVp dataset and a low kVp dataset. The high kVp dataset and low kVp set may be acquired, for example, using a fast-switching kVp technique as described hereinabove or any other dual energy method.

At 610, method 600 may include aligning high and low views in projection space. Aligning high and low views in projection space may include interpolating high and low data points in addition to time-aligning high and low kVp datasets as described herein above with regard to FIG. 5.

At 615, method 600 may include decomposing the aligned high and low datasets into a first material basis and a second material basis. Decomposition may be performed using, for example, basis material decomposition (BMD) wherein the measured projections are converted to a set of density line-integral projections as described herein above and known in the art. The material bases may comprise, for example, a water basis and an iodine basis. In other examples, the material bases may comprise different combinations of materials.

At 620, method 600 may include separating the first material basis and the second material basis into odd and even material basis projection datasets. Odd datasets may comprise aligned pairs of measured high kVp data and interpolated low kVp data while even datasets may comprise aligned pairs of measured low kVp data and interpolated high kVp data.

At 625, method 600 may include transforming the odd and even material basis projection datasets into corresponding odd and even material density images. Transforming the datasets into corresponding density images may comprise applying an image reconstruction algorithm, such as filtered back projection (FBP), to the datasets to transform the data from projection space to image space.

At 630, method 600 may include de-noising the odd and even material density images. De-noising the odd and even material density images may comprise applying a correlated noise reduction method, as known in the art.

At 635, method 600 may include applying a weight to each odd and even material density image and summing the odd and even pairs to generate a material density image for each material. Applying a weight to each odd and even material density image may comprise determining the sensitivity of material density to high and low energy projection data. As discussed herein above, material density may depend on the x-ray attenuation properties of the material. For example, the attenuation property of water remains constant to first order at high and low energy levels. As a result, water density images may be especially sensitive to high energy projection data. Therefore, odd water density images may be weighted more strongly than even water density images when generating a water density image. By weighting the odd and even material density images in this way when generating a material density image for a material, the image quality of the material density image may be improved. For example, the material density image may have improved contrast and resolution compared to a material density image generated without weighting, thereby improving the ability for an operator or a physician to discern features in the material density image.

At 640, method 600 may include summing the material density images for each material to generate a final monochromatic image.

It should be noted that ordering of steps in method 600 is provided as a non-limiting illustrative example. For example, in one embodiment, the datasets may be decomposed into material bases (e.g., step 615) prior to separating the decomposed datasets into odd and even datasets (e.g., step 620), as shown in FIG. 6. In another embodiment, the datasets may be separated into odd and even datasets (e.g., step 620) prior to decomposing the separated datasets into material bases (e.g., step 615).

Figure 7:
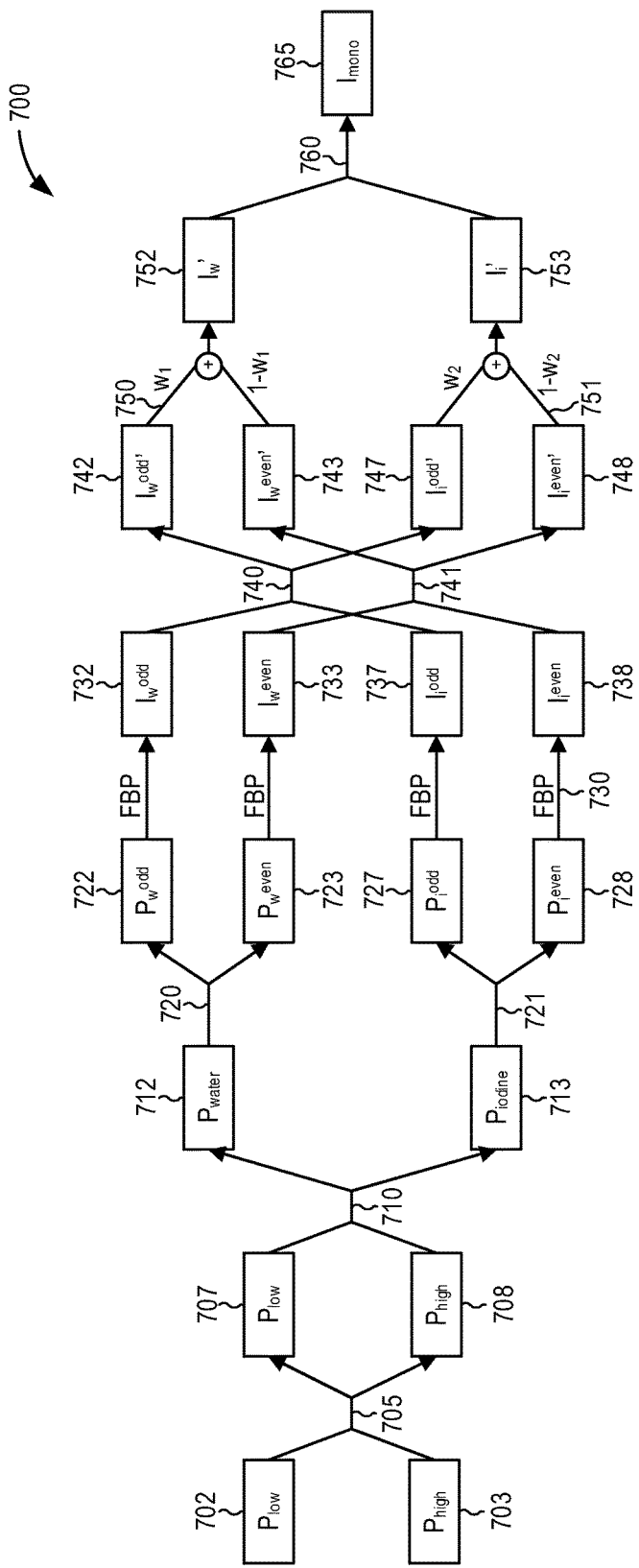
FIG. 7 shows a high-level block diagram illustrating an example method for weighting material density images when generating a monochromatic image according to an embodiment of the invention.

FIG. 7 shows a high-level block diagram illustrating an example technique 700 for weighting material density images when generating a monochromatic image according to an embodiment of the invention.

The low kVp projection dataset 702 and high kVp projection dataset 703 may be view-aligned at 705. Material decomposition 710 may separate the view-aligned low projection dataset 707 and the view-aligned high projection dataset 708 into a water projection dataset 712 and an iodine projection dataset 713.

The water projection dataset 712 may be separated 720 into an odd water projection dataset 722 and an even water projection dataset 723. The odd water projection dataset 722 may include the measured high kVp data and the interpolated low kVp data within the water projection dataset 712. The even water projection dataset 723 may include the measured low kVp data and the interpolated high kVp data within the water projection dataset 712.

Meanwhile, the iodine projection dataset 713 may be separated 721 into an odd iodine projection dataset 727 and an even iodine projection dataset 728. The odd iodine projection dataset 727 may include the measured high kVp data and interpolated low kVp data within the iodine projection dataset 713. The even iodine projection dataset 728 may include the measured low kVp data and the interpolated high kVp data within the iodine projection dataset 713.

Each of the odd and even material projection datasets 722, 723, 727, and 728 may be transformed 730 from projection space into image space to form corresponding odd and even material density images 732, 733, 737, and 738. Transformation 730 may comprise any image reconstruction method, including but not limited to filtered back projection.

The odd water density image 732 and the odd iodine density image 737 may undergo correlated noise reduction 740 to produce de-noised odd water density image 742 and de-noised odd iodine density image 747. Similarly, the even water density image 733 and the even iodine density image 738 may undergo correlated noise reduction 741 to produce de-noised even water density image 743 and de-noised even iodine density image 748.

The de-noised odd water density image 742 and the de-noised even water density image 743 may be summed 750 using weights to produce a de-noised water density image 752. In particular, the odd water density image 742 may be multiplied by a weighting function $w_1$ while the even water density image 743 may be multiplied by a weighting function $(1-w_1)$ prior to summing the density images. The value of $w_1$ determines the relative contribution of the odd water density image 742 and the even water density image 743 when generating the water density image 752. In this way, the value of $w_1$ may be selected to optimize the image quality of the water density image 752.

The de-noised odd iodine density image 747 and the de-noised even iodine density image 748 may be summed 751 using weights to produce a de-noised iodine density image 753. In particular, the odd iodine density image 747 may be multiplied by a weighting function $w_2$ while the even iodine density image 748 may be multiplied by a weighting function $(1-w_2)$ prior to summing the density images. The value of $w_2$ may determine the relative contribution of the odd iodine density image 747 and the even iodine density image 748 when generating the iodine density image 753. In this way, the value of $w_2$ may be selected to optimize the image quality of the iodine density image 753.

The optimized water density image 752 and the optimized iodine density image 753 may be combined 760 to generate a monochromatic image 765.

Figure 8:
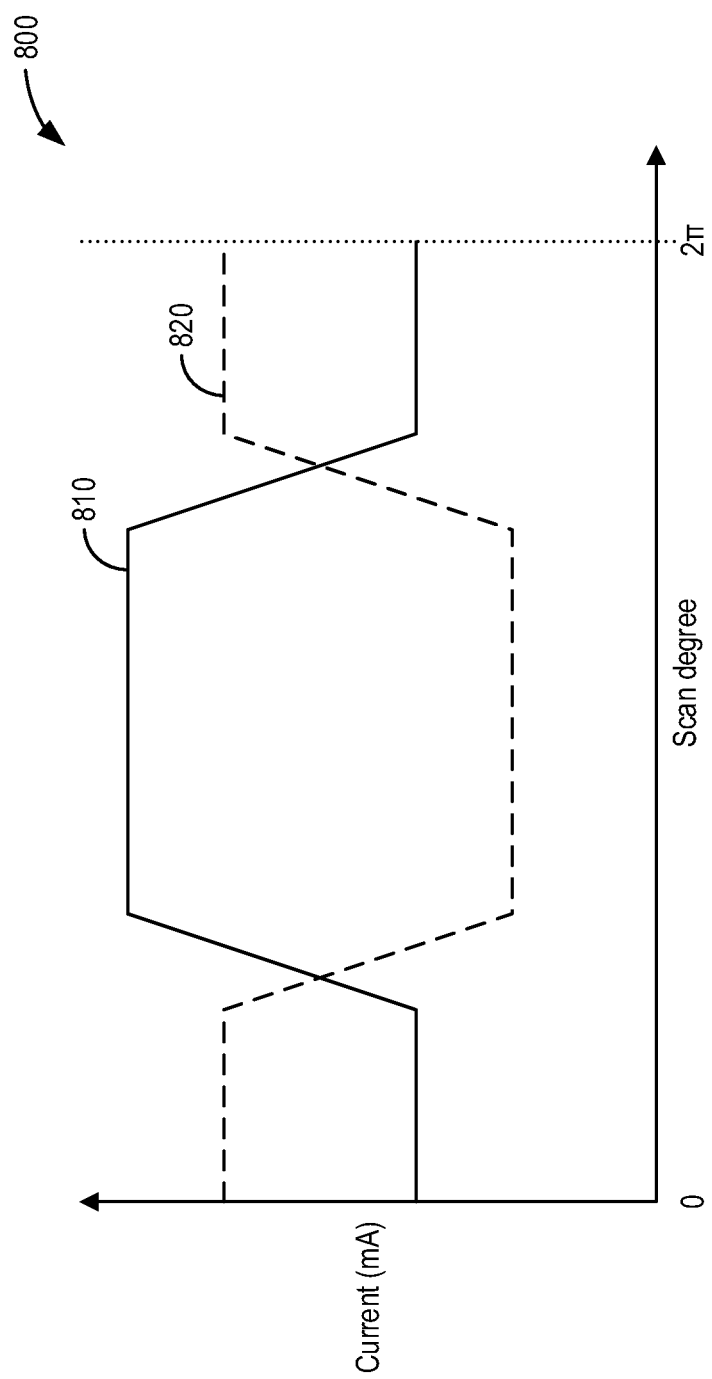
FIG. 8 shows a graph illustrating an example current modulation profile for rotate-rotate spectral imaging according to an embodiment of the invention.

FIG. 8 shows a graph 800 illustrating an example current modulation profile for rotate-rotate spectral imaging according to an embodiment of the invention. In particular, graph 800 depicts how the current driving the x-ray source 14 may be adjusted during scanning, thereby lowering radiation dosing of the imaged subject. Modulation profile 810 depicts a current profile for low energy scanning and modulation profile 820 depicts a current profile for high energy scanning.

For rotate-rotate spectral imaging, the detectors 20 may rotate 360 degrees about the rotational axis 24 twice, collecting high kVp projection data during the first rotation and low kVp projection data during the second rotation, or vice versa. As described herein above, a water density image may primarily comprise high kVp projection data, while an iodine density image may primarily comprise low kVp projection data. As the scan angle of the detector 20 increases through a full rotation, the current may increase or decrease depending on the task of the acquisition. For example, modulation profile 810 shows the current increasing to a maximum and then decreasing again while collecting low kVp projection data, while modulation profile 820 shows the current decreasing to a minimum and increasing again while collecting high kVp projection data. The weighting scheme described herein may subsequently weight the high or low projection data based on the modulated current profiles 810 and 820 to compensate for the reduced radiation dosing. Modulation profiles 810 and 820 may be contrasted with current profiles known in the art, wherein the current is typically constant over all scan degrees for both high and low kVp data acquisition. In this way, image quality may be maintained while reducing radiation dosing.

The technical effect of the disclosure may include a weighting of material density images generated by a dual energy CT imaging system. Another technical effect of the disclosure may include an improved image quality of images generated by a dual energy CT imaging system without increasing a radiation dosing.

In one embodiment, a method for dual energy imaging of a material comprises generating an odd material density image, generating an even material density image, applying a first weight to the odd material density image and a second weight to the even material density image, and generating a material density image based on a combination of the weighted odd material density image and the weighted even material density image. The odd material density image comprises measured high energy data and interpolated low energy data. The even material density image comprises measured low energy data and interpolated high energy data.

The first weight and the second weight may be based on an attenuation behavior of the material at high and low energies. In one example, the material is water and the first weight is greater than the second weight. For example, the first weight equals one and the second weight equals zero.

In another example, the material is iodine and the first weight is less than the second weight. For example, the first weight equals zero and the second weight equals one.

In some examples, the method further comprises applying a noise reduction to the odd material density image and the even material density image prior to applying the first weight and the second weight.

In another embodiment, a method for dual energy imaging comprises obtaining a first dataset based on incident high energy spectra and a second dataset based on incident low energy spectra, updating the first dataset with an interpolated high energy dataset and the second dataset with an interpolated low energy dataset, decomposing the updated first dataset and the updated second dataset into a first material basis and a second material basis, and separating the first material basis into a first odd subset and a first even subset and the second material basis into a second odd subset and a second even subset. In some examples, the method comprises separating the datasets into odd and even subsets prior to decomposing the odd and even subsets into material bases. The method further comprises transforming the first odd subset and the first even subset respectively into a first odd density image and a first even density image, and the second odd subset and the second even subset respectively into a second odd density image and a second even density image. The method further comprises applying a first weight to the first odd density image, a second weight to the first even density image, a third weight to the second odd density image, and a fourth weight to the second even density image. The method further comprises generating a first density image based on the weighted first odd density image and the weighted first even density image, and a second density image based on the weighted second odd density image and the weighted second even density image. The method further comprises generating a final monochromatic image based on the first density image and the second density image. In one example, the transformation comprises a filtered back projection.

In one example, the first weight is greater than the second weight, and the fourth weight is greater than the third weight. In another example, the first material basis is water and the second material basis is iodine.

In yet another embodiment, an imaging system comprises an x-ray source that emits a beam of x-rays toward an object to be imaged, a detector that receives the x-rays attenuated by the object, and a data acquisition system (DAS) operably connected to the detector. The imaging system further comprises a computer operably connected to the DAS and programmed to generate an odd material density image comprising measured high energy data received from the detector and interpolated low energy data, generate an even material density image comprising measured low energy data received from the detector and interpolated high energy data, apply a first weight to the odd material density image and a second weight to the even material density image, and generate a material density image based on a combination of the weighted odd material density image and the weighted even material density image.

In one example, the first weight and the second weight are based on an attenuation behavior of a material at high and low energies. In another example, the material is water and the first weight is greater than the second weight. In such an example, the first weight equals one and the second weight equals zero.

In another example, the material is iodine and the first weight is less than the second weight. In such an example, the first weight equals zero and the second weight equals one.

In one example, the computer is further programmed to apply a noise reduction to the odd material density image and the even material density image prior to applying the first weight and the second weight.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method for dual energy imaging of a material, comprising:
    generating, with a processor, an odd material density image;
    generating, with the processor, an even material density image, wherein the odd material density image and the even material density image are generated from measured high energy data, measured low energy data, and data interpolated by the processor from the measured high energy data and the measured low energy data;
    applying, with the processor, a first weight to the odd material density image and a second weight to the even material density image; and
    generating, with the processor, a material density image based on a combination of the weighted odd material density image and the weighted even material density image.

2. The method of claim 1, wherein the odd material density image comprises the measured high energy data and interpolated low energy data, the interpolated low energy data interpolated by the processor from the measured low energy data.

3. The method of claim 1, wherein the even material density image comprises the measured low energy data and interpolated high energy data, the interpolated high energy data interpolated by the processor from the measured high energy data.

4. The method of claim 1, wherein the first weight and the second weight are based on an attenuation behavior of the material at high and low energies.

5. The method of claim 1, wherein the material is water and the first weight is greater than the second weight.

6. The method of claim 5, wherein the first weight equals one and the second weight equals zero.

7. The method of claim 1, wherein the material is iodine and the first weight is less than the second weight.

8. The method of claim 7, wherein the first weight equals zero and the second weight equals one.

9. The method of claim 1, further comprising applying a noise reduction to the odd material density image and the even material density image prior to applying the first weight and the second weight.

10. An imaging system for dual energy imaging of a material, comprising:
    an x-ray source that emits a beam of x-rays toward an object to be imaged;
    a detector that receives the x-rays attenuated by the object;
    a data acquisition system (DAS) operably connected to the detector; and
    a computer operably connected to the DAS and configured with executable instructions in non-transitory memory that when executed cause the computer to:
        generate an odd material density image;
        generate an even material density image, wherein the odd material density image and the even material density image are generated from measured high energy data, measured low energy data, and data interpolated by the computer from the measured high energy data and the measured low energy data;
        apply a first weight to the odd material density image and a second weight to the even material density image; and
        generate a material density image based on a combination of the weighted odd material density image and the weighted even material density image.

11. The system of claim 10, wherein the odd material density image comprises the measured high energy data and interpolated low energy data, the interpolated low energy data interpolated by the computer from the measured low energy data.

12. The system of claim 10, wherein the even material density image comprises the measured low energy data and interpolated high energy data, the interpolated high energy data interpolated by the computer from the measured high energy data.

13. The system of claim 10, wherein the first weight and the second weight are based on an attenuation behavior of the material at high and low energies.

14. The system of claim 10, wherein the material is water and the first weight is greater than the second weight.

15. The system of claim 14, wherein the first weight equals one and the second weight equals zero.

16. The system of claim 10, wherein the material is iodine and the first weight is less than the second weight.

17. The system of claim 16, wherein the first weight equals zero and the second weight equals one.

18. The system of claim 10, wherein the computer is further configured with executable instructions in non-transitory memory that when executed cause the computer to apply a noise reduction to the odd material density image and the even material density image prior to applying the first weight and the second weight.

\* \* \* \* \*